(12) United States Patent
Tonegawa et al.

(10) Patent No.: US 8,178,722 B2
(45) Date of Patent: May 15, 2012

(54) METHOD FOR PRODUCING THEANINE

(75) Inventors: Fumio Tonegawa, Koshigaya (JP);
Kimio Ueda, Koshigaya (JP)

(73) Assignee: Junsei Chemical Co., Ltd., Tokyo (JP)

( * ) Notice: Subject to any disclaimer, the term of this patent is extended or adjusted under 35 U.S.C. 154(b) by 693 days.

(21) Appl. No.: 11/815,261

(22) PCT Filed: Feb. 1, 2006

(86) PCT No.: PCT/JP2006/301637
§ 371 (c)(1),
(2), (4) Date: Aug. 1, 2007

(87) PCT Pub. No.: WO2006/082835
PCT Pub. Date: Aug. 10, 2006

(65) Prior Publication Data
US 2008/0281123 A1    Nov. 13, 2008

(30) Foreign Application Priority Data
Feb. 4, 2005   (JP) ................. 2005-028556

(51) Int. Cl.
*C07C 229/00*   (2006.01)
*C12P 13/04*    (2006.01)
*C12P 13/14*    (2006.01)

(52) U.S. Cl. .................... 562/563; 435/106; 435/110

(58) Field of Classification Search .............. None
See application file for complete search history.

(56) References Cited

U.S. PATENT DOCUMENTS
4,761,495 A * 8/1988 Wirth et al. .................. 560/41

FOREIGN PATENT DOCUMENTS
JP    55 35059      3/1980
JP    2004 203822   7/2004
WO    97 28117      8/1997

OTHER PUBLICATIONS
W09728117 CAPLUS Abstract, 1997.*

JP2004-203822, machine translation (pp. 1-7).*

* cited by examiner

*Primary Examiner* — Daniel Sullivan
*Assistant Examiner* — Clinton Brooks
(74) *Attorney, Agent, or Firm* — Oblon, Spivak, McClelland, Maier & Neustadt, L.L.P.

(57) ABSTRACT

A method for producing theanine including reacting a glutamic acid alkyl ester represented by general Formula (1):

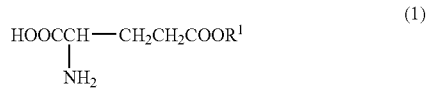

where $R^1$ represents an alkyl group, with a ketone represented by general Formula (2):

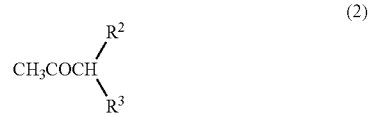

where $R^2$ represents a hydrogen atom, $R^3$ represents a lower alkanoyl group or a benzoyl group, and $R^2$ and $R^3$ may form a cycloalkanone ring in combination with the vicinal carbon atom, in the presence of t-butylamine, a secondary amine or a tertiary amine, reacting the resultant compound represented by general Formula (3):

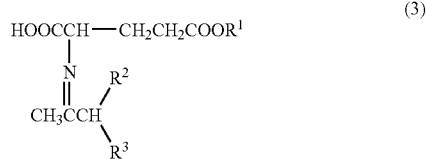

where $R^1$, $R^2$ and $R^3$ are the same as defined above, with ethylamine, and then being subjected to heating in the presence of the ethylamine or reaction with a fatty acid.

13 Claims, No Drawings

METHOD FOR PRODUCING THEANINE

TECHNICAL FIELD

The present invention relates to a method for producing theanine.

BACKGROUND ART

Theanine (L-glutamic acid-γ-ethylamide), which is known as an ingredient contributing to taste of green tea, has been elucidated to have various physiological actions such as a relaxing action, caffeine excitation suppressing action and hypotensive action. Thus, there is a great demand for theanine as a food additive. However, the content of theanine in green-tea leaves is extremely small. In the circumstances, a method for chemically synthesizing theanine has been desired.

Conventionally, in a known method for producing theanine, theanine is produced by reacting ethylamine with each of starting materials: N-trityl-L-glutamic acid-γ-benzylester obtained by protecting the γ-carboxyl group of L-glutamic acid by benzylation and the amino group thereof by tritylation (see Patent Document 1); N-substituted L-pyrolidone carboxylic acid (see Patent Document 2); a glutamic acid derivative obtained by protecting the α-amino group of glutamic acid by a Boc group and the carboxyl group thereof by an OtBu group (see Patent Document 3); and a glutamic acid anhydride obtained by protecting the α-amino group of the glutamic acid (see Patent Document 4); and thereafter, removing each protecting group.

However, the conventional method mentioned above has problems in that raw materials are expensive and product yields are low. It disadvantageously requires a number of steps and intricate operations associated with various chromatographic purification methods which lead to time-consuming work and high production costs. Due to these problems, it cannot be said that the conventional method is an industrially suitable production method. Furthermore, in consideration that the obtained theanine is used as a food additive, not only a method for producing highly purified theanine but also a method for producing theanine without using a harmful metal to human bodies has been desired.

[Patent Document 1] JP-A-5-70419
[Patent Document 2] JP-A-11-116542
[Patent Document 3] JP-A-2000-26383
[Patent Document 4] JP-A-2001-278848

DISCLOSURE OF THE INVENTION

Problems to be Solved by the Invention

In the circumstances, an object of the present invention is to provide a method for producing theanine, by which highly purified theanine can be obtained in high yield inexpensively in smaller numbers of steps.

Means for Solving the Problems

The present inventors intensively studied with the view toward solving the aforementioned problems. As a result, they found that when protection reaction of the α-amino group of an L-glutamic acid alkyl ester is performed not in the presence of a generally used substance such as an acid, inorganic base or dehydrating agent but in the presence of a predetermined amine to protect the α-amino group with a ketone, the amino group can be quantitatively protected while preventing production of pyroglutamic acid and hydrolysis of an ester group. Consequently, production of a metal salt in the case of using an inorganic base and a decrease in protection rate can be avoided. They further found that when deprotection reaction is performed by heating in the presence of excessive ethylamine or by adding a fatty acid, theanine alone can be selectively crystallized. Consequently, production of an inorganic salt by neutralization and purification with ion exchange or the like can be avoided and highly purified theanine can be produced in high yield. Based on the finding that highly purified theanine can be efficiently produced inexpensively in smaller numbers of steps by virtue of these improvements, they accomplished the present invention.

More specifically, the present invention relates to a method for producing theanine including reacting a glutamic acid alkyl ester represented by general Formula (1):

where $R^1$ represents an alkyl group,
with a ketone represented by general Formula (2):

where $R^2$ represents a hydrogen atom, $R^3$ represents a lower alkanoyl group or a benzoyl group, and $R^2$ and $R^3$ may form a cycloalkanone ring in combination with the vicinal carbon atom, in the presence of t-butylamine, a secondary amine or a tertiary amine, reacting the resultant compound represented by general Formula (3):

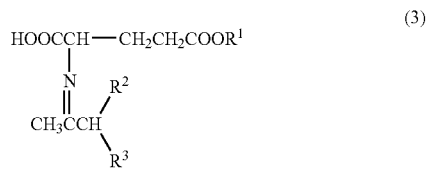

where $R^1$, $R^2$ and $R^3$ are the same as defined above,
with ethylamine, and then, being subjected to heating in the presence of the ethylamine or reaction with a fatty acid.

Effect of the Invention

According to the production method of the present invention, highly purified theanine can be produced inexpensively and easily in a simple operation as well as in good yield. The method is therefore suitable for industrial production. Furthermore, since a harmful metal or the like to human bodies is not used and the purity of the theanine obtained is extremely high, theanine can be used safely also as a food additive.

BEST MODE FOR CARRYING OUT THE INVENTION

The production method of the present invention includes the following reaction schemes using an L-glutamic acid alkyl ester (1) as a starting material.

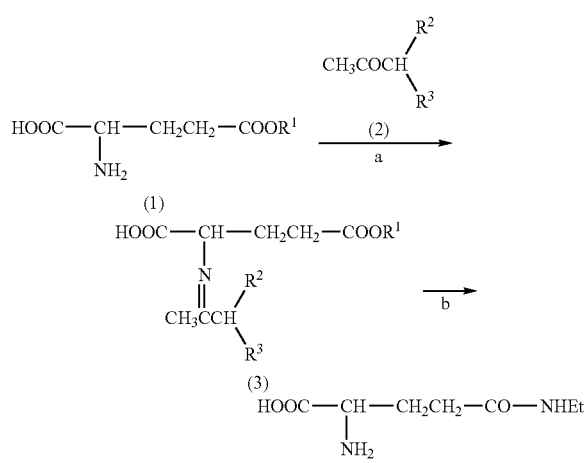

where $R^1$ represents an alkyl group, $R^2$ represents a hydrogen atom, $R^3$ represents a lower alkanoyl group or a benzoyl group, and $R^2$ and $R^3$ may form a cycloalkanone ring in combination with the vicinal carbon atom.

As the alkyl group represented by $R^1$ in the formula, a linear or branched alkyl group having 1 to 6 carbon atoms may be mentioned. Examples thereof may include a methyl group, ethyl group, propyl group, isopropyl group, butyl group, t-butyl group, pentyl group and hexyl group. Of them, a methyl group is particularly preferred.

As the lower alkanoyl group represented by $R^3$, an alkanoyl group having 2 to 6 carbon atoms may be mentioned. Examples thereof may include an acetyl group, propanoyl group and butanoyl group. Of them, an acetyl group is particularly preferred. As the cycloalkanone ring formed of $R^2$ and $R^3$ in combination with the vicinal carbon atom, a cycloalkanone ring having 3 to 6 carbon atoms may be mentioned. Examples thereof may include cyclopropanone, cyclopentanone and cyclohexanone. The ketone of a cycloalkanone ring is preferably present at the second position.

An L-glutamic acid alkyl ester (1) is a known compound and easily available by purchase on the market.

Each of the steps will be now described.

[Step a]

This is a step for reacting an L-glutamic acid alkyl ester (1) with a ketone (2) to protect the α-amino group. The reaction is performed in the presence of t-butyl amine, a secondary amine or a tertiary amine.

Examples of the secondary amine used in the reaction may include dimethylamine, diethylamine, diisopropylamine and N-methylaniline. Examples of the tertiary amine may include trimethylamine, triethylamine, tri-n-butylamine and N,N-dimethylaniline. Of them, triethylamine is particularly preferable.

The solvent to be used in the reaction is not particularly limited as long as it cannot adversely affect the reaction. Examples of the solvent may include an alcohol such as methanol or ethanol; an aromatic hydrocarbon such as benzene, toluene or xylene; an ether such as diethylether, tetrahydrofuran or dioxane; a halogenated hydrocarbon such as dichloromethane or chloroform. Of them, methanol and ethanol are preferable.

The ratio of the amine or ketone to be used herein relative to the L-glutamic acid alkyl ester (1) is preferably 1.0 to 2.0 equivalents, and particularly preferably, 1.0 to 1.5 equivalents.

The reaction temperature is not particularly limited, however, it is usually 50° C. to 100° C., and preferably, 60° C. to 70° C.

The reaction time is not particularly limited, however, it is usually 0.5 to 6 hours.

[Step b]

This is a step for performing deprotection of the α-amino group by reacting ethylamine to amidate the γ position of the compound represented by Formula (3) and obtained in the aforementioned step, and heating the resultant reaction product in the presence of excessive ethylamine or adding a fatty acid.

As the ethylamine to be used in the reaction, 100% anhydrous ethylamine, a commercially available 30 to 70% aqueous ethylamine solution and ethylamine hydrochloride may be used. In particular, a 70% aqueous ethylamine solution is preferably used. Ethylamine is preferably used in an amount 5 to 10 times as large as the reaction solution.

The reaction temperature is not particularly limited, however, it is usually 0° C. to 80° C., and preferably, 15° C. to 20° C.

The reaction time is not particularly limited, however, it is usually 3 to 24 hours, and preferably, 4 to 6 hours.

The obtained compound is concentrated under reduced pressure to remove excessive ethylamine and reacted with a fatty acid to remove a ketone, or heated in the presence of excessive ethylamine also to remove a ketone.

As the fatty acid to be used in the reaction, a lower fatty acid having 1 to 6 carbon atoms is preferred. Examples thereof may include formic acid, acetic acid and propionic acid. Preferably, formic acid and acetic acid, and particularly preferably, formic acid may be used.

The fatty acid is preferably used in an amount of 1.5 to 3.0 equivalents and, in particular, 2.0 to 2.5 equivalents relative to a compound represented by Formula (3).

After completion of the reaction, an organic solvent such as an alcohol is added, followed by crystallization. The crystallized product is filtrated and dried to obtain a highly purified theanine.

EXAMPLES

The present invention will now be described more specifically by way of examples; however, the present invention will not be limited only to the following examples.

Example 1

First, 20.0 g (0.124 mol) of L-glutamic acid-γ-methyl ester was suspended in 20 g of methanol. To this, 13.7 g (0.137 mol) of acetylacetone and 12.5 g (0.124 mol) of triethylamine were added. The mixture was stirred at 60° C. for one hour. Subsequently, 80 g (1.24 mol) of 70% ethylamine was added to the mixture. After the mixture was allowed to react for 6 hours, excessive ethylamine was distilled away under reduced pressure. To this, 11.4 g (0.246 mol) of formic acid and 120 mL of 2-propanol (IPA) were added. The crystal precipitated was filtrated by suction and washed with 20 mL of IPA to obtain wet matter. The wet matter was dried under reduced pressure to obtain 17.7 g of theanine as a white crystal substance (yield: 82%).

The theanine thus obtained was tested for purification. As a result, the specific rotation was $[\alpha]D20=+8.1$ (C=5, water) and the hyperchloride titer was 100.1%. It was confirmed that the theanine has a high purity satisfying the standard value of L-theanine defined in the official formulary of food additives.

Example 2

First, 20.0 g (0.124 mol) of L-glutamic acid-γ-methyl ester was suspended in 20 g of methanol. To this, 13.7 g (0.137 mol) of acetylacetone and 12.5 g (0.124 mol) of triethylamine were added. The mixture was stirred at 60° C. for one hour. Subsequently, 80 g (1.24 mol) of 70% ethylamine was added to the mixture. After the mixture was allowed to react for 6 hours, excessive ethylamine was distilled away under reduced pressure. To this, 29.8 g (0.496 mol) of acetic acid, 30 mL of water and 120 mL of IPA were added. The mixture was heated for one hour and cooled on ice. The crystal precipitated was filtered by suction and washed with 20 mL of IPA to obtain wet matter. The wet matter was dried under reduced pressure to obtain 13.1 g of theanine as a white crystal substance (yield: 61%). The obtained theanine had the same purity as high as in Example 1.

Example 3

First, 320 g (1.983 mol) of L-glutamic acid-γ-methyl ester was suspended in 500 g of methanol. To this, 219 g (2.186 mol, 1.1 eq.) of acetylacetone and 200 g (1.983 mol, 1 eq.) of triethylamine were added. The mixture was stirred at 60° C. for one hour. Subsequently, 1,277 g (19.8 mol) of 70% ethylamine was added to the mixture. After the mixture was allowed to react for 6 hours, the reaction solution was heated under normal pressure. In this manner, 667 g of excessive ethylamine was recovered and deprotection was performed at the same time. To the slurry of the theanine precipitated, 1 L of 2-propanol was added. The crystal was filtrated by suction and washed with 200 mL of 99.5% ethanol to obtain theanine (314.3 g) as a white crystal substance (yield: 91%). The obtained theanine had the same purity as high as in Example 1.

Example 4

First, 5.0 g (31 mmol) of L-glutamic acid-γ-methyl ester was suspended in 15 mL of methanol. To this, 3.4 g (34 mmol) of acetylacetone and 2.3 g (31 mmol) of t-butylamine were added. The mixture was heated at 60° C. for 2 hours. Subsequently, 20 g (310 mmol) of 70% ethylamine was added to the mixture and the same procedure as in Example 1 was performed to obtain 3.6 g of theanine (yield: 66.7%). The obtained theanine had the same purity as high as in Example 1.

Example 5

First, 5.0 g (31 mmol) of L-glutamic acid-γ-methyl ester was suspended in 15 mL of methanol. To this, 3.4 g (34 mmol) of acetylacetone and 3.1 g (31 mmol) of diisopropylamine were added. The mixture was heated at 60° C. for 2 hours. Subsequently, 20 g (310 mmol) of 70% ethylamine was added to the mixture and the same procedure as in Example 1 was performed to obtain 4.1 g of theanine (yield: 75.9%). The obtained theanine had the same purity as high as in Example 1.

Example 6

First, 5.0 g (31 mmol) of L-glutamic acid-γ-methyl ester was suspended in 15 mL of methanol. To this, 3.4 g (34 mmol) of acetylacetone and 5.7 g (31 mmol) of tri-n-butylamine were added. The mixture was heated at 60° C. for 2 hours. Subsequently, 20 g (310 mmol) of 70% ethylamine was added to the mixture and the same procedure as in Example 1 was performed to obtain 3.6 g of theanine (yield: 66.7%). The obtained theanine had the same purity as high as in Example 1.

Example 7

First, 5.0 g (31 mmol) of L-glutamic acid-γ-methyl ester was suspended in 15 mL of methanol. To this, 4.3 g (34 mmol) of 2-acetyl-cyclopentanone and 3.1 g (31 mmol) of triethylamine were added. The mixture was heated at 60° C. for 2 hours. Subsequently, 20 g (310 mmol) of 70% ethylamine was added to the mixture and the same procedure as in Example 1 was performed to obtain 3.6 g of theanine (yield: 66.7%). The obtained theanine had the same purity as high as in Example 1.

Example 8

First, 5.0 g (31 mmol) of L-glutamic acid-γ-methyl ester was suspended in 15 mL of methanol. To this, 5.6 g (34 mmol) of 1-phenyl-1,3-butanediol and 3.1 g (31 mmol) of triethylamine were added. The mixture was heated at 60° C. for 2 hours. Subsequently, 20 g (310 mmol) of 70% ethylamine was added to the mixture and the same procedure as in Example 1 was performed to obtain 4.7 g of theanine (yield: 87%). The obtained theanine had the same purity as high as in Example 1.

Comparative Example 1

First, 5.0 g (31 mmol) of L-glutamic acid-γ-methyl ester was suspended in 45 g of toluene. To this, 15 g (233 mmol) of acetylacetone and 5.6 g (93 mmol) of acetic acid were added. The mixture was heated for 2 hours while removing water generated by use of an ester tube at 100° C. to 110° C. The solvent was removed to obtain 7.9 g of a yellow oily substance. To the oily substance, 13.5 g (210 mmol) of 70% ethylamine was added and allowed to react for 23 hours. The same procedure as in Example 1 was performed to obtain 0.2 g of theanine (yield: 5.5%).

Comparative Example 2

First, 5.0 g (31 mmol) of L-glutamic acid-γ-methyl ester was suspended in 25 mL of methanol. To this, 5.0 g (26 mmol) of a 28% methanol solution of sodium methylate was added dropwise. After completion of the dropwise addition, excessive L-glutamic acid-γ-methyl ester was filtrated off and 3.1 g (31 mmol) of acetylacetone and 5.0 g of anhydrous sodium sulfate were added. The mixture was heated at 60° C. for 3 hours. Subsequently, sodium sulfate was filtrated off. To the filtrate, 20 g (310 mmol) of 70% ethylamine was added. After the mixture was allowed to react for 6 hours, excessive ethylamine was distilled away under reduced pressure. Subsequently, 8 mL (140 mmol) of formic acid and 30 mL of 2-propanol (IPA) were added. The crystal precipitated was filtrated by suction and washed with 20 mL of IPA to obtain wet matter. The wet matter was dried under reduced pressure to obtain 3.8 g of crystal containing theanine. When the crystal was titered by hyperchloride, the content of theanine was 80%. The crystal contains 20% of sodium formate. The crystal was recrystallized from water/methanol to obtain 1.6 g of theanine (yield: 30%).

Comparative Example 3

First, 5.0 g (31 mmol) of L-glutamic acid-γ-methyl ester was suspended in 15 mL of methanol. To this, 3.4 g (34 mmol)

of acetylacetone, 1.9 g (31 mmol) of acetic acid, and 5.0 g of anhydrous sodium sulfate were added. The mixture was heated at 60° C. for 2 hours. Subsequently, sodium sulfate was filtrated off. To the filtrate, 20 g (310 mmol) of 70% ethylamine was added and the same procedure as in Example 1 was performed to obtain 1.6 g of theanine (yield: 29.6%).

Comparative Example 4

First, 5.0 g (31 mmol) of L-glutamic acid-γ-methyl ester was suspended in 15 mL of methanol. To this, 3.4 g (34 mmol) of acetylacetone and 5.0 g of anhydrous sodium sulfate were added. The mixture was heated at 60° C. for 6 hours. Subsequently, sodium sulfate was filtrated off. To the filtrate, 20 g (310 mmol) of 70% ethylamine was added and the same procedure as in Example 1 was performed to obtain 2.0 g of theanine (yield: 37.0%).

As is described in Comparative Examples 1 to 4, when a protection reaction was performed in the presence of an acid such as acetic acid (Comparative Example 1), an inorganic base such as sodium methylate (Comparative Example 2), an acid and a dehydrating agent (Comparative Example 3) or a dehydrating agent (Comparative Example 4), theanine was obtained in a yield as low as 5.5 to 37% or a poorly purified theanine was only obtained. In contrast, according to the method of the present invention, theanine having purity sufficiently capable of being used as a food additive can be obtained in quite high yield by, for example, subjecting a reaction mixture to a simple treatment such as washing with alcohol.

The invention claimed is:

1. A method for producing theanine which avoids production of a metal salt and consists essentially of:
    (a) reacting in the presence of t-butylamine, a secondary amine or a tertiary amine:
        (1) a glutamic acid alkyl ester represented by general Formula (1):

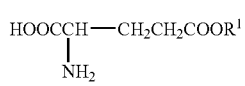
(1)

where R¹ represents an alkyl group, with
    (2) a ketone represented by general Formula (2):

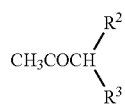
(2)

where R² represents a hydrogen atom, R³ represents a lower alkanoyl group or a benzoyl group, and R² and R³ may form a cycloalkanone ring in combination with the vicinal carbon atom;
    (b) reacting the step (a) reaction product represented by general Formula (3):

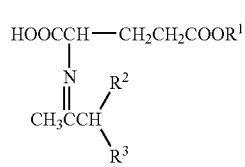
(3)

where R¹, R² and R³ are the same as defined above, with ethylamine; and then
    (c) heating the step (b) reaction product in the presence of ethylamine or reacting the step (b) reaction product with a fatty acid;
    wherein the method does not comprise production of metal salts or purification steps to remove metal salts, and theanine is produced in yields of from 61 to 91%.

2. The method according to claim 1, wherein R³ is an acetyl group.

3. The method according to claim 1 or 2, wherein step (c) is reacting the step (b) reaction product with a fatty acid and the fatty acid is formic acid or acetic acid.

4. The method according to claim 1, wherein R¹ is a linear or branched alkyl group having 1 to 6 carbon atoms.

5. The method according to claim 1, wherein R³ is an alkanoyl group having 2 to 6 carbon atoms.

6. The method according to claim 1, wherein the secondary amine in step (a) is selected from the group consisting of dimethylamine, diethylamine, diisopropylamine and N-methylaniline.

7. The method according to claim 1, wherein the tertiary amine in step (a) is selected from the group consisting of trimethylamine, triethylamine, tri-n-butylamine and N,N-dimethylaniline.

8. The method according to claim 1, wherein step (c) is heating the step (b) reaction product in the presence of ethylamine and the ethylamine is used in an amount 5 to 10 times as large as the reaction solution.

9. The method according to claim 1, wherein step (c) is reacting the step (b) reaction product with a fatty acid.

10. The method according to claim 1, wherein step (c) is heating the step (b) reaction product in the presence of ethylamine.

11. A method for producing theanine comprising:
    (a) reacting in the presence of t-butylamine, a secondary amine or a tertiary amine:
        (1) a glutamic acid alkyl ester represented by general Formula (1):

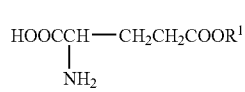
(1)

where R¹ represents an alkyl group, with
    (2) a ketone represented by general Formula (2):

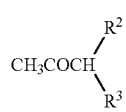
(2)

where R² represents a hydrogen atom, R³ represents a lower alkanoyl group or a benzoyl group, and R² and R³ may form a cycloalkanone ring in combination with the vicinal carbon atom;

(b) reacting the step (a) reaction product represented by general Formula (3):

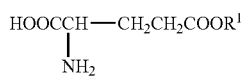
(3)

where $R^1$, $R^2$ and $R^3$ are the same as defined above, with an excessive amount of ethylamine; and then (c) heating the step (b) reaction product in the presence of excessive ethylamine;

wherein the method does not comprise production of metal salts or purification steps to remove metal salts, and theanine is produced in yields of from 61 to 91%.

12. A method for producing theanine comprising:

(a) reacting in the presence of t-butylamine, a secondary amine or a tertiary amine:

(1) a glutamic acid alkyl ester represented by general Formula (1):

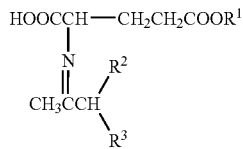
(1)

where $R^1$ represents an alkyl group, with (2) a ketone represented by general Formula (2):

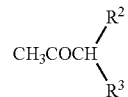
(2)

where $R^2$ represents a hydrogen atom, $R^3$ represents a lower alkanoyl group or a benzoyl group, and $R^2$ and $R^3$ may form a cycloalkanone ring in combination with the vicinal carbon atom;

(b) reacting the step (a) reaction product represented by general Formula (3):

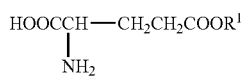
(3)

where $R^1$, $R^2$ and $R^3$ are the same as defined above, with ethylamine; and then (c) reacting the step (b) reaction product with a fatty acid in an amount of 1.5 to 3.0 equivalents relative to the step (a) reaction product represented by general Formula (3);

wherein the method does not comprise production of metal salts or purification steps to remove metal salts, and theanine is produced in yields of from 61 to 91%.

13. The method according to claim 12, wherein step (c) is reacting the step (b) reaction product with a fatty acid in an amount of 2.0 to 2.5 equivalents relative to the step (a) reaction product represented by general Formula (3).

* * * * *